(12) United States Patent
Cheng et al.

(10) Patent No.: US 7,108,708 B2
(45) Date of Patent: Sep. 19, 2006

(54) METHOD FOR PLACING A MEDICAL AGENT INTO A VESSEL OF THE BODY

(75) Inventors: Eric Cheng, Miami, FL (US); Larry Dominguez, West Miami, FL (US)

(73) Assignee: Cordis Neurovascular, Inc., Miami Lakes, FL (US)

( * ) Notice: Subject to any disclaimer, the term of this patent is extended or adjusted under 35 U.S.C. 154(b) by 233 days.

(21) Appl. No.: 10/681,403

(22) Filed: Oct. 8, 2003

(65) Prior Publication Data

US 2004/0068289 A1    Apr. 8, 2004

Related U.S. Application Data

(63) Continuation of application No. 09/955,396, filed on Sep. 18, 2001, now abandoned.

(51) Int. Cl.
*A61M 29/00* (2006.01)
*A61M 31/00* (2006.01)

(52) U.S. Cl. .................... 606/200; 604/93.01

(58) Field of Classification Search ........... 606/200; 604/57, 500
See application file for complete search history.

(56) References Cited

U.S. PATENT DOCUMENTS

| | | | |
|---|---|---|---|
| 2,688,329 A | 9/1954 | Wallace | |
| 4,790,331 A | 12/1988 | Okada et al. | |
| 5,108,407 A | 4/1992 | Geremia et al. | |
| 5,122,136 A | 6/1992 | Guglielmi et al. | |
| 5,263,964 A | 11/1993 | Purdy | |
| 5,334,210 A | 8/1994 | Gianturco | |
| 5,350,397 A | 9/1994 | Palermo et al. | |
| 5,382,259 A | 1/1995 | Phelps et al. | |
| 5,464,395 A | 11/1995 | Faxon et al. | |
| 5,667,493 A | 9/1997 | Janacek | |
| 5,776,114 A | 7/1998 | Frantzen et al. | |
| 5,779,669 A | 7/1998 | Haissaguerre et al. | |
| 5,836,957 A | 11/1998 | Schulz et al. | |
| 5,846,223 A | 12/1998 | Swartz et al. | |
| 5,853,418 A | 12/1998 | Ken et al. | |
| 5,873,842 A | 2/1999 | Brennen et al. | |
| 5,885,238 A | 3/1999 | Stevens et al. | |
| 5,911,725 A | 6/1999 | Boury | |
| 5,916,194 A | 6/1999 | Jacobsen et al. | |
| 6,033,423 A | 3/2000 | Ken et al. | |
| 6,113,622 A | 9/2000 | Hieshima | |
| 6,126,649 A | 10/2000 | VanTassel et al. | |
| 6,179,857 B1 | 1/2001 | Diaz et al. | |
| 6,183,491 B1 | 2/2001 | Lulo | |
| 6,572,628 B1 | 6/2003 | Dominguez et al. | |
| 2003/0055450 A1 | 3/2003 | Cheng et al. | |

OTHER PUBLICATIONS

U.S. Appl. No. 09/894,421, E. Cheng, et al.
U.S. Appl. No. 10/681,602, E. Cheng, et al.

*Primary Examiner*—(Jackie) Tan-Uyen T. Ho
(74) *Attorney, Agent, or Firm*—Henry W. Collins

(57) ABSTRACT

A method for placing an embolic coil into an aneurysm utilizing a delivery system having a deflected distal section. The delivery system stabilizes an embolic coil deployment system thereby placing the embolic coil with greater accuracy.

2 Claims, 3 Drawing Sheets

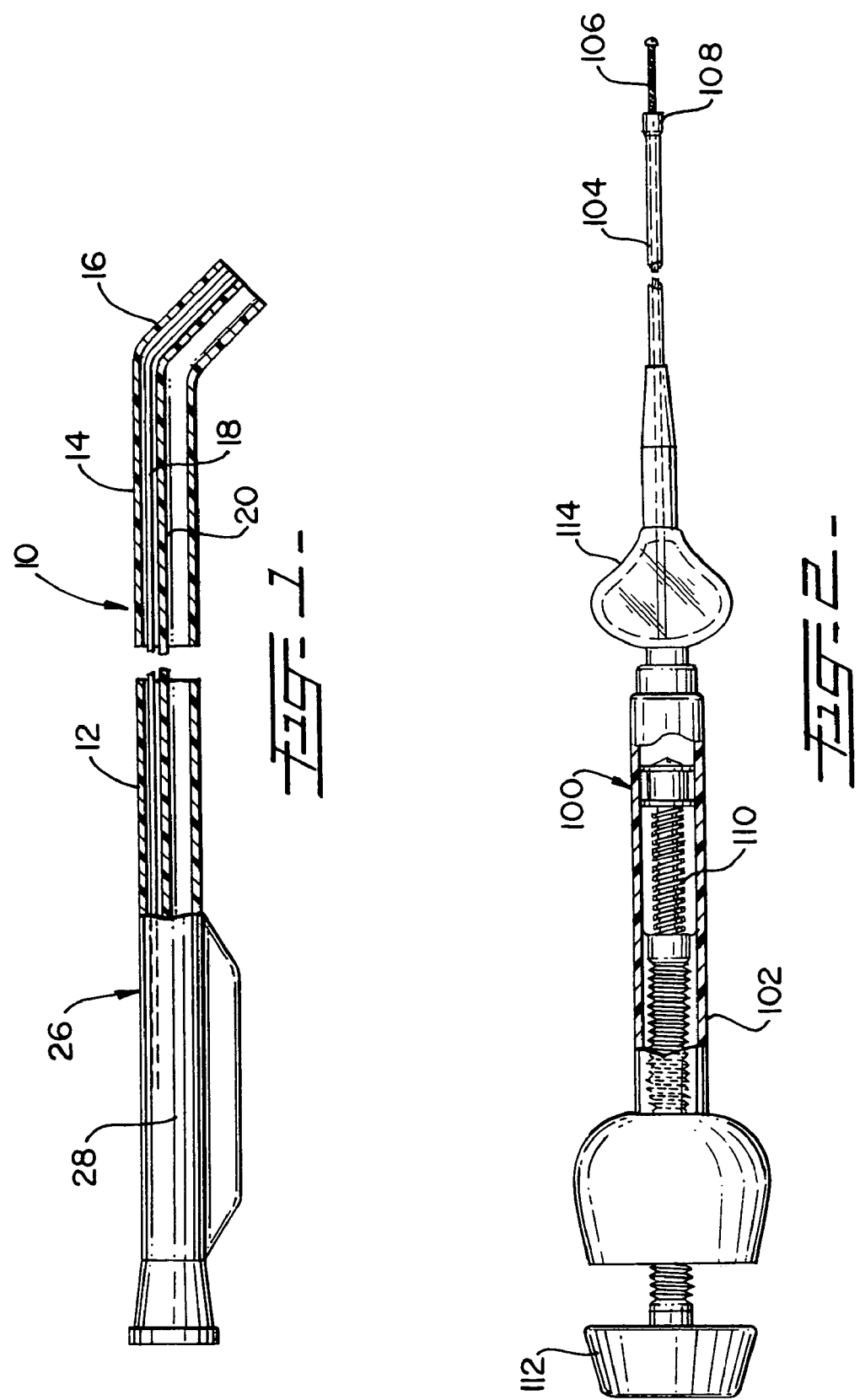

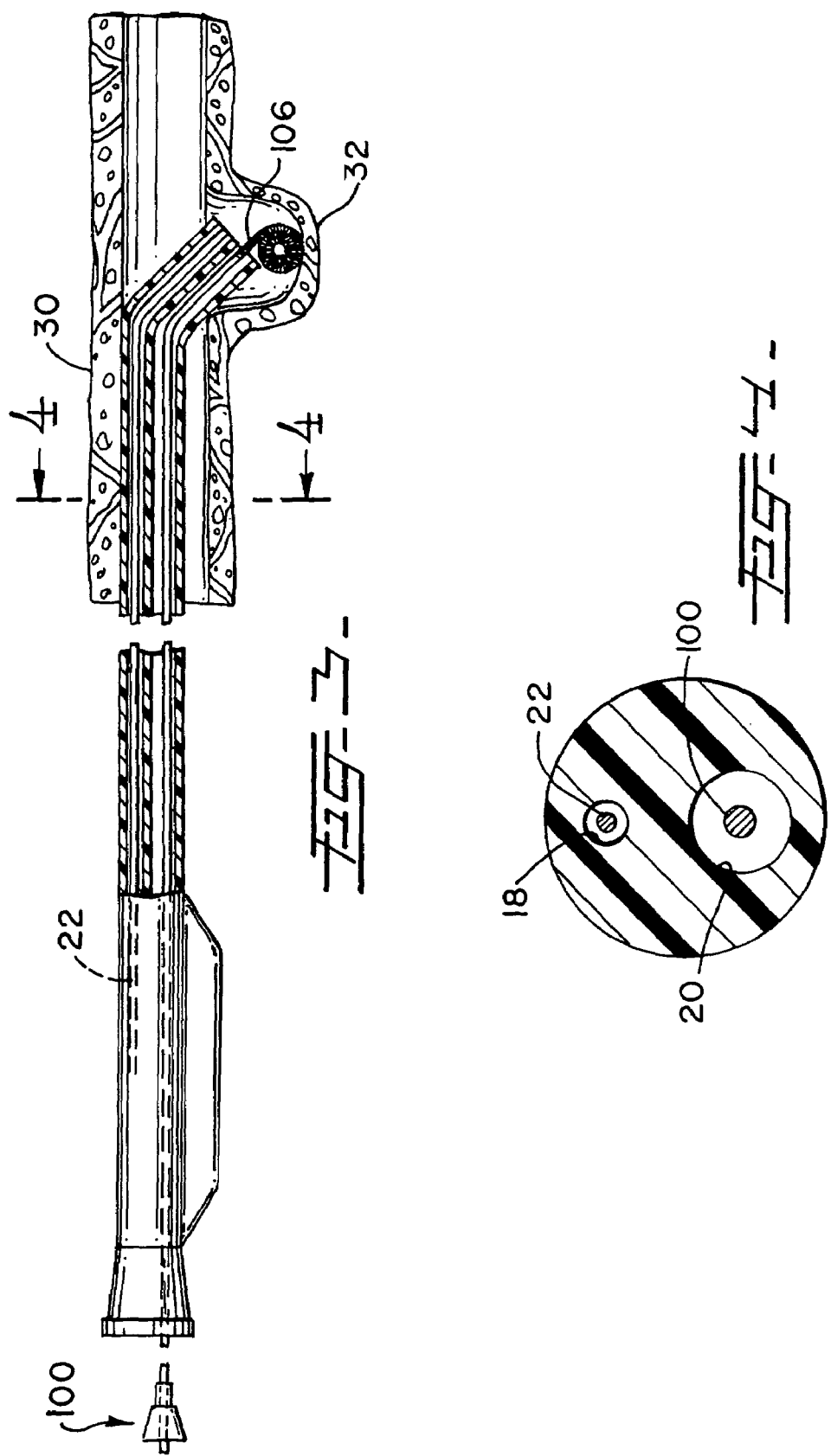

METHOD FOR PLACING A MEDICAL AGENT INTO A VESSEL OF THE BODY

This application is a continuation of 09/955,396 filed Sep. 18, 2001, which is abandoned.

BACKGROUND OF THE INVENTION

1. Field of the Invention

This invention concerns a novel method for placing a medical agent into a vessel of a patient, in particular, placing embolic coils into an aneurysm of the brain.

2. Description of the Prior Art

For many years physicians have been placing various devices within a blood vessel of the human body in order to treat aneurysms or to occlude a vessel at a particular location. Such devices are placed within the aneurysm or vessel using a deployment system. When a device is deployed into the vessel but misses its intended position, it is difficult, if not impossible to retrieve or reposition the device. To help alleviate this problem, a delivery system is employed to increase the probability of placing the device precisely at a pre-selected position. A variety of delivery systems exist to provide stability and increase deployment accuracy. The combination of different devices, deployment systems, and delivery systems provide physicians with reliable methods of treating aneurysms.

Various types of devices are placed within an aneurysm or a vessel to occlude the flow of blood through the vessel by promoting thrombus formation at a particular location. Such devices include dilation balloons, radiopaque fluids, liquid medications, and embolic coils. Embolic coils may take the form of helically wound coils, randomly wound coils, coils wound within other coils, or many other coil configurations. These coils are generally formed of radiopaque metallic materials, such as platinum, gold, and tungsten, or alloys of these metals. Often times, several coils are placed at a given location in order to occlude the flow of blood through the vessel.

One example of an embolic coil design is disclosed in U.S. Pat. No. 6,179,857 entitled, "Stretch Resistant Embolic Coil With Variable Stiffness." The coil is a helically wound coil in which various combinations of adjacent turns are spot welded together to create a stretch resistant coil of a pre-selected flexibility. Another coil configuration is disclosed in U.S. Pat. No. 6,183,491 entitled, "Embolic Coil Deployment System With Improved Embolic Coil," which shows an embolic coil having a relatively flexible proximal portion which resists stretching.

Also, U.S. Pat. No. 5,853,418 entitled, "Stretch Resistant Vaso-occlusive Coils," discloses a helically wound coil having a polymeric stretch resisting member extending through the lumen of the coil and fixedly attached to both the distal end and the proximal end of the coil. Other examples of coil configurations are disclosed in U.S. Pat. No. 5,334,210 entitled, "Vascular Occlusion Assembly" and U.S. Pat. No. 5,382,259 entitled, "Vasoocclusion Coil With Attached Tubular Woven Or Braided Fibrous Covering." With all coil designs, it is important that embolic coils remain very flexible for traveling through vessels when used with deployment systems.

A variety of deployment systems are available for placing embolic coils within an aneurysm or vessel. An example of such a system is disclosed in U.S. Pat. No. 6,113,622 entitled, "Embolic Coil Hydraulic Deployment System," assigned to the same assignee as the present patent application. The disclosure of the above patent is incorporated into and made part of this patent application. The hydraulic embolic coil deployment system uses fluid pressure which is applied to the distal section of the deployment catheter for expanding the distal section radially to release the embolic coil at a pre-selected position.

Another coil deployment system utilizes a deployment catheter having a socket at the distal end for retaining a ball which is bonded to the proximal end of the coil. The ball is placed in the socket within a lumen at the distal end of the deployment catheter, and the deployment system is then moved into a vessel to place the coil at a desired position. Then, a pusher wire with a piston at the end is pushed distally from the proximal end of the deployment catheter to thereby push the ball out of the socket and release the coil at the desired position. This system is disclosed in U.S. Pat. No. 5,350,397 entitled, "Axially Detachable Embolic Coil Assembly."

Also, U.S. Pat. No. 5,263,964 entitled, "Coaxial Traction Detachment Apparatus And Method," discloses another coil deployment system. This system uses glue or solder for attaching the embolic coil to a guidewire which is, in turn, placed within a flexible deployment catheter for positioning the coil within the vessel at a pre-selected position. Once the coil is at the desired position, the coil is restrained by the deployment catheter, and the guidewire is pulled from the proximal end of the deployment catheter causing the coil to be detached from the guidewire and released from the deployment system.

Examples of other deployment systems are disclosed in U.S. Pat. No. 5,122,136 entitled, "Endovascular Electrolytically Detachable Guidewire Tip For The Electroformation Of Thrombus In Arteries, Veins, Aneurysms, Vascular Malformations And Arteriovenous Fistulas" and U.S. Pat. No. 5,108,407 entitled, "Method And Apparatus For Placement Of An Embolic Coil." Even though fluoroscopic visualization shows physicians general movement of an embolic coil through the vasculature of the body and the use of coil deployment systems allow physicians to control when the embolic coil is released, it is still difficult to precisely place a coil at a pre-selected location, such as a location within an aneurysm. However, with the use of a delivery system, it is possible to stabilize the deployment system within a vessel in order to more precisely place an embolic coil.

An example of such a delivery system is disclosed in U.S. patent application Ser. No. 09/894,735, entitled "Method And Apparatus For Placing A Medical Agent Into A Vessel Of The Body," filed on Jun. 28, 2001 and in U.S. patent application Ser. No. 09/894,421, entitled, "Method And Apparatus For Placing A Medical Agent Into A Vessel Of The Body," filed on Jun. 28, 2001, both assigned to the same assignee as the present patent application. These patent applications are incorporated by reference and are made a part of the present patent application. The delivery catheter disclosed in this patent application has two lumens. The first lumen has a shape retaining wire which extends therethrough for shaping an intermediate section of the delivery catheter into a generally U-shaped configuration. The second lumen has a side opening at a location within the intermediate section of the delivery catheter. The side opening is positioned over an aneurysm, and then the embolic coil deployment system is inserted through the second lumen and into a position proximal the aneurysm. The U-shaped delivery catheter stabilizes the deployment system as the embolic coil is released into the aneurysm.

Another delivery system used to stabilize a coil deployment system is disclosed in U.S. patent application Ser. No. 09/878,530 entitled, "Delivery System Using Balloon Catheter," filed on Jun. 11, 2001 and assigned to the same assignee as the present patent application. The delivery catheter disclosed in this patent application includes a balloon adjacent to the distal end and an inflation port at the proximal end of the catheter for inflating the balloon. The delivery catheter is positioned within the vessel of a patient, and the balloon is inflated to stabilize the position of the delivery catheter. Then, an embolic coil deployment system is introduced into the delivery catheter and through a side opening of the catheter to deliver the embolic coil into the aneurysm.

When physicians use a delivery system in combination with a coil deployment system, the delivery system stabilizes the coil deployment system, and the coil may be placed with greater accuracy. Therefore, it is an objective of this invention to provide a method for placing embolic coils with increased accuracy. Furthermore, it is an objective to provide a system which is relatively simple in construction and easy to use.

SUMMARY OF THE INVENTION

In accordance with one aspect of the present invention, a method is provided for placing an embolic agent into an aneurysm. The method includes the use of a delivery catheter having a proximal section, an intermediate section, and a distal section which is formed from a flexible polymeric material. The delivery catheter includes a first lumen, a second lumen, and a pre-shaped retaining wire which extends through the first lumen to form a normally deflected distal section. The method includes the steps of inserting a straightening wire into the second lumen of the delivery catheter to cause the normally deflected distal section of the delivery catheter to become relatively straight, introducing the delivery catheter into a vessel of a patient to a position where the normally deflected distal section is generally aligned with the aneurysm, withdrawing the straightening wire from the second lumen of the delivery catheter to cause the normally deflected distal section to again become deflected and thereby move to a position proximate to the aneurysm, introducing an embolic agent deployment system into the second lumen of the delivery catheter and through the normally deflected distal section. The method also includes the steps of delivering the embolic agent into the aneurysm with the embolic coil deployment system, withdrawing the embolic agent deployment system from the delivery catheter, again inserting the straightening wire into the second lumen of the delivery catheter to cause the normally deflected distal section to become relatively straight, and thereafter withdrawing the delivery catheter from the vessel of the patient.

In accordance with a similar aspect of the present invention, the embolic agent deployment system takes the form of an embolic coil deployment system, and the embolic agent takes the form of an embolic coil.

In accordance with another aspect of the present invention, a method is provided for placing an embolic agent into an aneurysm. This method includes the use of a delivery catheter having a proximal section, an intermediate section, and a distal section which is formed from a flexible polymeric material. The delivery catheter includes a first lumen, a second lumen, and a shape retaining wire which extends through the first lumen. The method also includes the use of an embolic agent deployment system having an elongated, flexible deployment catheter with a lumen extending therethrough. The deployment catheter includes a distal section being formed of a material with a durometer which exhibits the characteristic that when a fluid pressure is applied to the lumen the walls of the distal section of the deployment catheter expand radially. The deployment catheter also includes a source of pressure coupled to the proximal section for applying a fluid pressure to the lumen and an embolic agent being disposed in fluid-tight engagement with the lumen of the distal section. The method includes the steps of shaping the distal section of the delivery catheter to form a normally deflected distal section, inserting a straightening wire into the second lumen of the delivery catheter to cause the normally deflected distal section of the delivery catheter to become relatively straight, introducing the delivery catheter into a vessel of a patient to a position where the normally deflected distal section is generally aligned with the aneurysm, withdrawing the straightening wire from the second lumen of the delivery catheter to cause the normally deflected distal section to again become deflected and thereby move to a position proximate to the aneurysm, introducing an embolic agent deployment system into the second lumen of the delivery catheter and through the normally deflected distal section. The method also includes the step of applying fluid pressure to the lumen of the embolic agent deployment system thereby causing the walls of the distal section of the embolic agent deployment system to expand and release the embolic agent. Finally, the method includes withdrawing the embolic agent deployment system from the delivery catheter, again inserting the straightening wire into the second lumen of the delivery catheter to cause the normally deflected distal section to become relatively straight, and thereafter withdrawing the delivery catheter from the vessel of the patient.

In accordance with a similar aspect of the present invention, the embolic agent deployment system takes the form of an embolic coil deployment system, and the embolic agent takes the form of an embolic coil.

In accordance with still another aspect of the present invention, a method is provided for placing an embolic agent into an aneurysm. The method includes the use of a delivery catheter having a proximal section, an intermediate section, and a distal section which is formed from a flexible polymeric material. The delivery catheter includes a lumen and a normally deflected distal section which is pre-shaped. The method includes the steps of inserting a straightening wire into the lumen of the delivery catheter to cause the normally deflected distal section of the delivery catheter to become relatively straight, introducing the delivery catheter into a vessel of a patient to a position where the normally deflected distal section is generally aligned with the aneurysm, withdrawing the straightening wire from the lumen to cause the normally deflected distal section to again become deflected and thereby move to a position proximate to the aneurysm, introducing an embolic agent deployment system into the lumen of the delivery catheter and through the normally deflected distal section. The method also includes the steps of delivering the embolic agent into the aneurysm with the embolic agent deployment system, withdrawing the embolic agent deployment system from the delivery catheter, again inserting the straightening wire into the lumen of the delivery catheter to cause the normally deflected distal section to become relatively straight, and thereafter withdrawing the delivery catheter from the vessel of the patient.

In accordance with a similar aspect of the present invention, the embolic agent deployment system takes the form of an embolic coil deployment system, and the embolic agent takes the form of an embolic coil.

In accordance with another aspect of the present invention, a method is provided for placing an embolic coil into an aneurysm or vessel. The method includes the use of a delivery catheter having a proximal section, an intermediate section, and a distal section which is formed from a flexible polymeric material. The delivery catheter includes a lumen and a distal section which is shape retaining. The method includes the steps of shaping the distal section of the delivery catheter to form a normally deflected distal section, inserting a straightening wire into the lumen of the delivery catheter to cause the normally deflected distal section of the delivery catheter to become relatively straight, introducing the delivery catheter into a vessel of a patient to a position where the normally deflected distal section is generally aligned with the aneurysm, withdrawing the straightening wire from the lumen of the delivery catheter to cause the normally deflected distal section to again become deflected and thereby move to a position proximate to the aneurysm, introducing an embolic agent deployment system into the lumen of the delivery catheter and through the normally deflected distal section. The method also includes the steps of delivering the embolic agent into the aneurysm with the embolic agent deployment system, withdrawing the embolic agent deployment system from the delivery catheter, again inserting the straightening wire into the lumen of the delivery catheter to cause the normally deflected distal section to become relatively straight, and thereafter withdrawing the delivery catheter from the vessel of the patient.

In accordance with a similar aspect of the present invention, the embolic agent deployment system takes the form of an embolic coil deployment system, and the embolic agent takes the form of an embolic coil.

In accordance with still another aspect of the present invention, a method is provided for placing an embolic agent into an aneurysm. This method includes the use of a delivery catheter having a proximal section, an intermediate section, and a distal section which is formed from a relatively flexible polymeric material. The delivery catheter includes a first lumen and a second lumen. The method includes the steps of inserting a straightening wire into the second lumen of the delivery catheter, inserting a pre-shaped retaining wire into the first lumen of the delivery catheter to form a normally deflected distal section, introducing the delivery catheter into a vessel of a patient to a position where the normally deflected distal section is generally aligned with the aneurysm, withdrawing the straightening wire from the second lumen of the delivery catheter to cause the normally deflected distal section to again become deflected and thereby move to a position proximate to the aneurysm, introducing an embolic agent deployment system into the second lumen of the delivery catheter and through the normally deflected distal section. The method also includes delivering the embolic agent into the aneurysm with the embolic agent deployment system, withdrawing the embolic agent deployment system from the delivery catheter, again inserting the straightening wire into the second lumen of the delivery catheter to cause the normally deflected distal section to become relatively straight, and thereafter withdrawing the delivery catheter from the vessel of the patient.

In accordance with a similar aspect of the present invention, the embolic agent deployment system takes the form of an embolic coil deployment system, and the embolic agent takes the form of an embolic coil.

In accordance with another aspect of the present invention, a method is provided for placing an embolic agent into an aneurysm. This method includes the use of a delivery catheter having a proximal section, an intermediate section, and a distal section which is formed from a relatively flexible polymeric material. The delivery catheter includes a first lumen and a second lumen. The method includes the steps of inserting a shape retaining wire into the first lumen of the delivery catheter, shaping the distal section of the delivery catheter to form a normally deflected distal section, inserting a straightening wire into the second lumen of the delivery catheter to cause the normally deflected distal section of the delivery catheter to become relatively straight, introducing the delivery catheter into a vessel of a patient to a position where the normally deflected distal section is generally aligned with the aneurysm, withdrawing the straightening wire from the second lumen of the delivery catheter to cause the normally deflected distal section to again become deflected and thereby move to a position proximate to the aneurysm, introducing an embolic agent deployment system into the second lumen of the delivery catheter and through the normally deflected distal section. The method also includes delivering the embolic agent into the aneurysm with the embolic agent deployment system, withdrawing the embolic agent deployment system from the delivery catheter, again inserting the straightening wire into the second lumen of the delivery catheter to cause the normally deflected distal section to become relatively straight, and thereafter withdrawing the delivery catheter from the vessel of the patient.

In accordance with a similar aspect of the present invention, the embolic agent deployment system takes the form of an embolic coil deployment system, and the embolic agent takes the form of an embolic coil.

In accordance with still another aspect of the present invention, a method is provided for placing a medical agent into a vessel. The method includes the use of a delivery catheter having a proximal section, an intermediate section, and a distal section which is formed from a flexible polymeric material. The delivery catheter includes a first lumen, a second lumen, and a pre-shaped retaining wire which extends through the first lumen to form a normally deflected distal section. The method includes the steps of inserting a straightening wire into the second lumen of the delivery catheter to cause the normally deflected distal section of the delivery catheter to become relatively straight, introducing the delivery catheter into the vessel of a patient to a position where the normally deflected distal section is generally aligned with a pre-selected position within the vessel, withdrawing the straightening wire from the second lumen of the delivery catheter to cause the normally deflected distal section to again become deflected and thereby move to the pre-selected position within the vessel, introducing a medical agent deployment system into the second lumen of the delivery catheter and through the normally deflected distal section. The method also includes the steps of delivering the medical agent into the vessel with the medical agent deployment system, withdrawing the medical agent deployment system from the delivery catheter, again inserting the straightening wire into the second lumen of the delivery catheter to cause the normally deflected distal section to become relatively straight, and thereafter withdrawing the delivery catheter from the vessel of the patient.

In accordance with another aspect of the present invention, a method is provided for placing a medical agent into a vessel. The method includes the use of a delivery catheter having a proximal section, an intermediate section, and a distal section which is formed from a flexible polymeric material. The delivery catheter includes a lumen and a normally deflected distal section which is pre-shaped. The method includes the steps of inserting a straightening wire into the lumen of the delivery catheter to cause the normally deflected distal section of the delivery catheter to become relatively straight, introducing the delivery catheter into the vessel of a patient to a position where the normally deflected distal section is generally aligned with a pre-selected position within the vessel, withdrawing the straightening wire from the lumen to cause the normally deflected distal section to again become deflected and thereby move to the pre-selected position within the vessel, introducing a medical agent deployment system into the lumen of the delivery catheter and through the normally deflected distal section. The method also includes the steps of delivering the medical agent into the vessel with the medical agent deployment system, withdrawing the medical agent deployment system from the delivery catheter, again inserting the straightening wire into the lumen of the delivery catheter to cause the normally deflected distal section to become relatively straight, and thereafter withdrawing the delivery catheter from the vessel of the patient.

In accordance with still another aspect of the present invention, a method is provided for placing a medical agent into a vessel. This method includes the use of a delivery catheter having a proximal section, an intermediate section, and a distal section which is formed from a relatively flexible polymeric material. The delivery catheter includes a first lumen and a second lumen. The method includes the steps of inserting a straightening wire into the second lumen of the delivery catheter, inserting a pre-shaped retaining wire into the first lumen of the delivery catheter to form a normally deflected distal section, introducing the delivery catheter into a vessel of a patient to a position where the normally deflected distal section is generally aligned with a pre-selected position within the vessel, withdrawing the straightening wire from the second lumen of the delivery catheter to cause the normally deflected distal section to again become deflected and thereby move to the pre-selected position within the vessel, introducing a medical agent deployment system into the second lumen of the delivery catheter and through the normally deflected distal section. The method also includes delivering the medical agent into the vessel with the medical agent deployment system, withdrawing the medical agent deployment system from the delivery catheter, again inserting the straightening wire into the second lumen of the delivery catheter to cause the normally deflected distal section to become relatively straight, and thereafter withdrawing the delivery catheter from the vessel of the patient.

BRIEF DESCRIPTION OF THE DRAWINGS

FIG. 1 is an enlarged, partially sectioned view of a delivery catheter having a normally deflected distal section;

FIG. 2 is a partially sectioned view showing an embolic coil deployment system used with the delivery catheter of FIG. 1 to deploy an embolic coil;

FIG. 3 is an enlarged, partially sectioned view of the delivery catheter in use to deploy an embolic coil into an aneurysm;

FIG. 4 is a cross-sectional view of the delivery catheter, taken along the plane of the line 4—4' of FIG. 3; and, FIGS. 5–8 are diagrammatic sequential views of a method of placing embolic coils within an aneurysm.

DESCRIPTION OF THE PREFERRED EMBODIMENT

Figure 5:
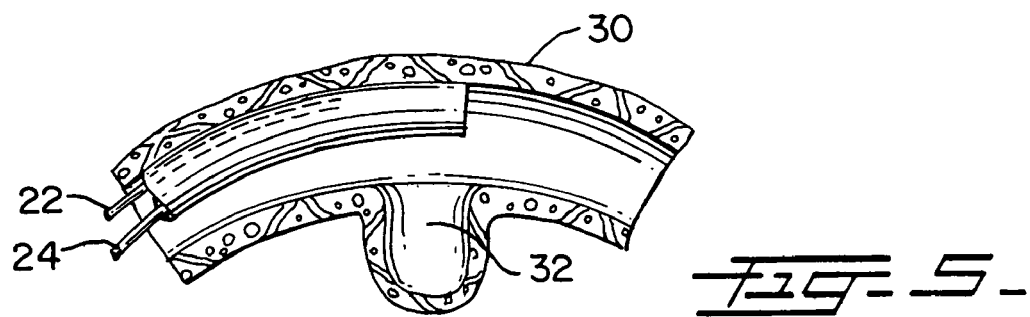

FIG. 1 illustrates a preferred embodiment of the delivery catheter of the present invention which generally includes a delivery catheter 10 connected to the distal end of a connector 26. More particularly, the delivery catheter 10 includes a first lumen 18 and a second lumen 20. The first lumen 18 extends from the proximal end to the distal end of the delivery catheter 10 and includes a pre-shaped retaining wire 22. The pre-shaped retaining wire 22 is bent proximal of the distal section 16 thereby causing the distal section 16 to be deflected angularly away from the center line of the delivery catheter 10. The second lumen 20 extends the entire length of the delivery catheter 10 and communicates with a lumen 28 which extends from the proximal end to the distal end of the connector 26.

While the delivery catheter 10 may be constructed of various flexible materials including various polymers, the delivery catheter 10 is preferably formed in three different sections with materials having different durometers and different polymer compositions. The proximal section 12 of the delivery catheter 10 is preferably formed of a nylon material having a durometer of approximately 75D and extends for a length of about 100 centimeters. The intermediate section 14 is preferably formed of a nylon material having a durometer of approximately 65D and extends for a length of about 40 centimeters. The distal section 16 is preferably formed of a polyurethane material having a durometer of approximately 80AE and is about 5 centimeters in length. With this construction the delivery catheter 10 is sufficiently flexible to be introduced through the various tortuous vessels of the human brain but at the same time provides sufficient rigidity for inserting the delivery catheter into and through these vessels. This construction also makes possible the ease of deflection of the distal section 16.

FIG. 2 illustrates a hydraulic embolic coil deployment system 100 which is comprised of a hydraulic injector, or syringe 102, coupled to the proximal end of a deployment catheter 104. An embolic coil 106 is disposed within the lumen at the distal section 108 of the deployment catheter. The proximal end of the coil 106 is tightly held within the lumen of the distal section 108 until the deployment device is activated for release of the coil. As shown, the syringe 102 includes a threaded piston 110 which is controlled by the handle 112 for infusing fluid into the interior of the deployment catheter 104. Also, as illustrated, the deployment catheter 104 includes a winged hub 114 which aids in the insertion of the deployment catheter 104.

Preferably, the distal section 108 of the deployment catheter 104 is formed of a polymeric material with a relatively low durometer which exhibits the characteristic that, when a fluid pressure of approximately 90 to 450 psi is applied to the interior of the deployment catheter, the walls of the distal section 108 expand radially, to thereby release the proximal end of the embolic coil 106. A more detailed description of the hydraulic embolic coil deployment system is disclosed in U.S. Pat. No. 6,113,622, assigned to the same assignee as the present patent application.

FIG. 3 illustrates, in detail, the delivery catheter 10 which has been inserted into a blood vessel 30 of the brain. The pre-shaped retaining wire 22 extends through the first lumen 18, and the distal section 16 is deflected to generally align with the aneurysm 32. The embolic coil deployment system 100 is shown inserted through the second lumen 20 of the delivery catheter 10 in order to place an embolic coil 106 into an aneurysm 32.

FIG. 4 illustrates a cross-sectional view taken through the delivery catheter 10 at a location indicated by 4—4' shown in FIG. 3. More particularly, FIG. 4 illustrates the location where the pre-shaped retaining wire 22 extends through the first lumen 18. Also illustrated is an end view of the embolic coil deployment system 100 which passes through the second lumen 20 of the delivery catheter 10.

Figure 6:
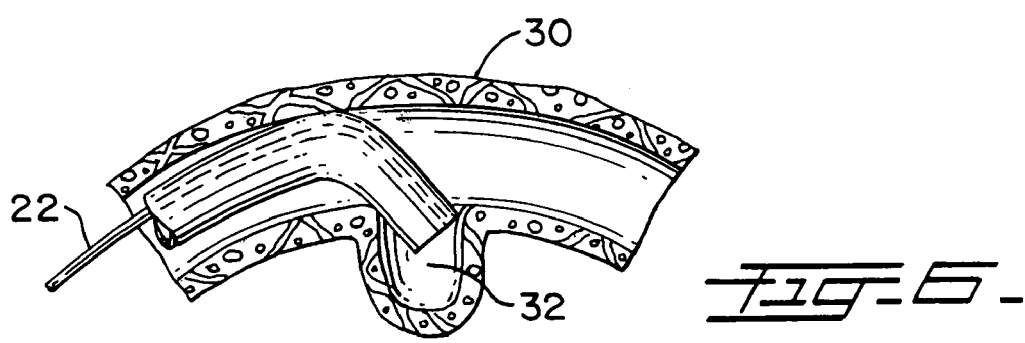
Figure 7:
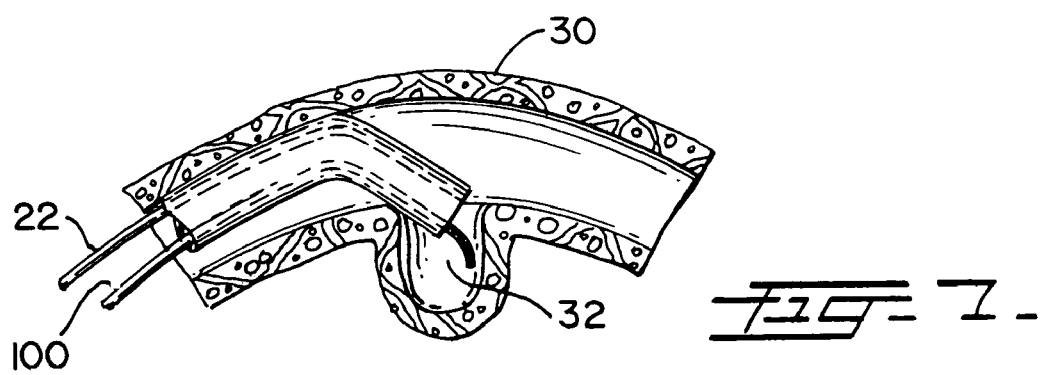
Figure 8:
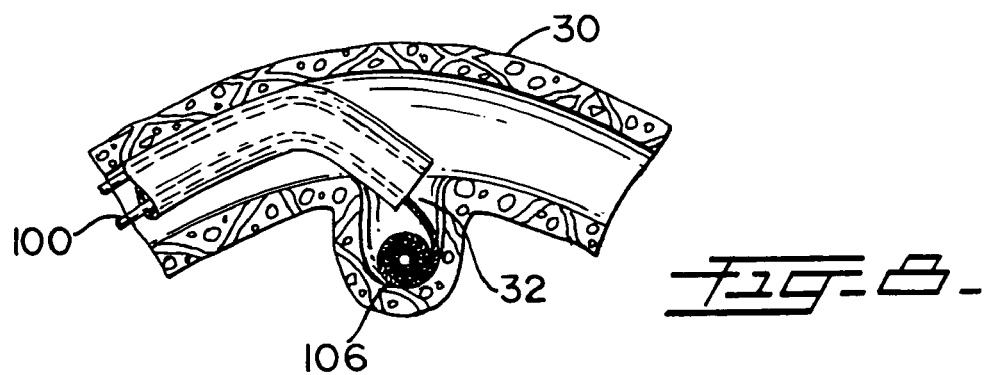

FIGS. 5 through 8 are provided for an understanding of the operation of the delivery catheter 10 used in conjunction with the embolic coil deployment system 100. As illustrated in FIG. 5, the delivery catheter 10 is inserted into a vessel 30 over a straightening wire 24 in the second lumen 20. The delivery catheter 10 is then positioned such that the distal section 16 is generally aligned with the aneurysm 32. Next, the straightening wire 24 is removed, and as illustrated in FIG. 6, the distal section 16 of the delivery catheter 10 normally deflects thereby causing the distal section 16 to move to a position proximate to the aneurysm 34. Once the distal section 16 has been positioned, the embolic coil deployment system 100 may then be inserted into the second lumen 20 and through the distal section 16 as illustrated in FIG. 7. Then, the embolic coil 106 may be placed into the aneurysm 32 and released from the deployment system 100 as illustrated in FIG. 8. The deployment system 100 may then be removed, and this process may be repeated until a sufficient number of embolic coils 106 have been placed into the aneurysm 32. When the aneurysm 32 has been sufficiently filled with embolic coils, the coil deployment system 100 may be removed from the delivery catheter 10. Thereafter, the straightening wire 24 may be again inserted into the second lumen 20 thereby causing the distal section 16 of the delivery catheter 10 to straighten within the vessel. Then, the delivery catheter 10 may be easily withdrawn from the vessel 30 and from the body of the patient.

A novel system has been disclosed in which an embolic coil is delivered precisely to a pre-selected position. Although a preferred embodiment of the invention has been described, it is to be understood that various modifications may be made by those skilled in the art without departing from the scope of the present invention. For example, instead of delivering an embolic coil to an aneurysm, a medical agent may be placed within a vessel.

Also, the delivery catheter may be constructed with a shape retaining wire disposed in the first lumen. In this case a physician may shape the distal section into a deflected configuration prior to use.

In another alternative construction, the delivery catheter may be comprised of a single lumen having neither a pre-shaped retaining wire nor a shape retaining wire. Instead, the delivery catheter is formed of a shape retaining polymer which may be heat set to deflect the distal section, either by the manufacturer or by the physician prior to use.

Furthermore, a pre-shaped retaining wire or a shape retaining wire could be inserted into a dual lumen catheter. By introducing either wire into a lumen of the delivery catheter, the manufacturer or physician could deflect the distal section.

In a final alternative construction, the sections of the delivery catheter could be sections of a unitary structure with changing durometers.

These and other modifications would be apparent to those having ordinary skill in the art to which this invention relates and are intended to be within the scope of the claims which follow.

The invention claimed is:

1. A method for placing an embolic agent into an aneurysm comprising the steps of:

providing a delivery catheter having a proximal section, an intermediate section, and a distal section which is formed from a relatively flexible polymeric material, the delivery catheter having a first lumen and a second lumen, and the delivery catheter having a shape retaining wire extending through the first lumen;

providing an embolic agent deployment system having an elongated, flexible deployment catheter with a lumen extending therethrough, the deployment catheter having a distal section being formed of a material with a durometer which exhibits the characteristic that when a fluid pressure is applied to the lumen the walls of the distal section of the deployment catheter expand radially, the deployment catheter having a source of pressure coupled to the proximal section for applying a fluid pressure to the lumen, and the deployment catheter having an embolic agent being disposed in fluid-tight engagement within the lumen of the distal section;

shaping the distal section of the delivery catheter to form a normally deflected distal section;

inserting a straightening wire into the second lumen of the delivery catheter to cause the normally deflected distal section of the delivery catheter to become relatively straight;

introducing the delivery catheter into a vessel of a patient to a position where the normally deflected distal section is generally aligned with the aneurysm;

withdrawing the straightening wire from the second lumen of the delivery catheter to cause the normally deflected distal section to again become deflected and thereby move to a position proximate to the aneurysm;

introducing the embolic agent deployment system into the second lumen of the delivery catheter and through the normally deflected distal section;

applying fluid pressure to the lumen of the embolic agent deployment system thereby causing the walls of the distal section of the embolic agent deployment system to expand and release the embolic agent;

withdrawing the embolic agent deployment system from the delivery catheter;

again inserting the straightening wire into the second lumen of the delivery catheter to cause the normally deflected distal section to become relatively straight; and, thereafter withdrawing the delivery catheter from the vessel of the patient.

2. A method as defined in claim 1, wherein the embolic agent deployment system is an embolic coil deployment system and the embolic agent is an embolic coil.

* * * * *